(12) United States Patent
Morningstar

(10) Patent No.: US 7,867,162 B2
(45) Date of Patent: Jan. 11, 2011

(54) IMPLANTABLE FLUID DEVICES

(75) Inventor: Randy L. Morningstar, Brooklyn Park, MN (US)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 12/418,616

(22) Filed: Apr. 6, 2009

(65) Prior Publication Data
US 2009/0253953 A1 Oct. 8, 2009

(30) Foreign Application Priority Data
Apr. 7, 2008 (DK) ............................... 2008 00503

(51) Int. Cl.
*A61F 5/00* (2006.01)
*A61B 19/00* (2006.01)
(52) U.S. Cl. ........................................ 600/38; 128/897
(58) Field of Classification Search ............. 600/38–41, 600/37; 128/897, 898
See application file for complete search history.

(56) References Cited

U.S. PATENT DOCUMENTS

| | | | |
|---|---|---|---|
| 4,009,711 A * | 3/1977 | Uson ........................... 600/40 |
| 4,066,073 A | 1/1978 | Finney et al. |
| 4,201,202 A * | 5/1980 | Finney et al. ................. 600/40 |
| 4,318,396 A | 3/1982 | Finney |
| 4,342,308 A * | 8/1982 | Trick ........................... 600/40 |
| 4,353,360 A | 10/1982 | Finney et al. |
| 4,399,811 A | 8/1983 | Finney et al. |
| 4,411,260 A | 10/1983 | Koss |
| 4,523,584 A | 6/1985 | Yachia et al. |
| 4,550,720 A | 11/1985 | Trick |
| 4,558,693 A | 12/1985 | Lash et al. |
| 4,651,721 A | 3/1987 | Mikulich et al. |
| 4,665,903 A | 5/1987 | Whitehead |
| 4,773,403 A | 9/1988 | Daly |
| 4,820,270 A * | 4/1989 | Hardcastle et al. ....... 604/96.01 |
| 4,829,990 A | 5/1989 | Thüroff et al. |
| 4,852,555 A | 8/1989 | Trick |
| 4,881,531 A | 11/1989 | Timm et al. |
| 4,895,139 A | 1/1990 | Hauschild et al. |
| 5,067,485 A | 11/1991 | Cowen |
| 5,087,246 A * | 2/1992 | Smith ..................... 604/103.13 |
| 5,101,813 A | 4/1992 | Trick |
| 5,226,887 A * | 7/1993 | Farr et al. ............... 604/103.09 |
| 5,318,587 A * | 6/1994 | Davey ........................ 606/194 |
| 5,456,666 A * | 10/1995 | Campbell et al. ...... 604/103.08 |

(Continued)

FOREIGN PATENT DOCUMENTS

CA 1134554 11/1982

(Continued)

*Primary Examiner*—Samuel G Gilbert
(74) *Attorney, Agent, or Firm*—Coloplast Corp., Coloplast A/S; Daniel G. Chapik; Nicholas R. Baumann

(57) ABSTRACT

An implantable fluid device comprises a flexible fluid chamber capable of being in an inflated state and a deflated state. The chamber has a first end, a second end, and a central longitudinal axis from the first end to the second end. The chamber also has, in cross section when deflated, a plurality of alternating protrusions and intermediate portions about the central longitudinal axis. When deflated, the protrusions have a selected height and the intermediate portions have a selected depth. When inflated, the protrusions have the selected height and the intermediate portions have a selected height.

6 Claims, 3 Drawing Sheets

U.S. PATENT DOCUMENTS

| | | |
|---|---|---|
| 5,518,499 A | 5/1996 | Agar |
| 5,766,151 A * | 6/1998 | Valley et al. .......... 604/103.07 |
| 5,895,424 A | 4/1999 | Steele, Sr. et al. |
| 6,013,055 A * | 1/2000 | Bampos et al. ........ 604/103.07 |
| 6,780,366 B2 * | 8/2004 | Vang et al. .................. 264/301 |
| 2003/0212463 A1 | 11/2003 | Seo |
| 2003/0220539 A1 | 11/2003 | George et al. |
| 2004/0021505 A1 | 2/2004 | Watanabe |
| 2004/0225182 A1 | 11/2004 | Eid |
| 2005/0113639 A1 | 5/2005 | George et al. |
| 2006/0079836 A1 | 4/2006 | Holman et al. |
| 2006/0235267 A1 * | 10/2006 | George et al. ................. 600/40 |
| 2007/0175487 A1 | 8/2007 | Eid |
| 2009/0105530 A1 | 4/2009 | Kuyava |
| 2009/0124851 A1 | 5/2009 | Kuyava |

FOREIGN PATENT DOCUMENTS

| | | |
|---|---|---|
| DE | 3918955 | 12/1989 |
| DE | 3918955 A1 | 12/1989 |
| WO | 8601398 A1 | 3/1986 |
| WO | 9114409 A1 | 10/1991 |

* cited by examiner

IMPLANTABLE FLUID DEVICES

FIELD OF THE INVENTION

The present invention relates generally to implantable fluid devices. The invention relates specifically to implantable fluid reservoirs for inflatable penile prostheses, and to implantable, inflatable cylinders for inflatable penile prostheses.

BACKGROUND OF THE INVENTION

Inflatable penile prostheses (or, as may be termed hereinafter, "IPPs") are well known and have been in wide use. These devices are surgically implanted in male patients who, typically, are unable to achieve or sustain a penile erection due to a physical disability.

IPPs typically comprise several components such as a fluid reservoir, a pump, a valve, at least one inflatable cylinder, and various lengths of tubing which fluidly connect the fluid reservoir, the pump, the valve, and the inflatable cylinder or cylinders (hereinafter, whether singular or plural, "cylinder"). Typically the fluid reservoir is surgically implanted in the patient's abdomen, with the pump and the inflatable cylinder being surgically implanted in, respectively, the patient's scrotum and penile corpora cavernosa; and the valve is commonly co-located with the scrotal pump. After implantation and in use, when an erection is desired by the patient, the scrotal pump is typically manipulated by the patient in an instructed way to cause fluid transfer from the reservoir, via the valve, to the cylinder such that inflation of the cylinder is effected thereby resulting in an erection as desired. When the patient desires to terminate the erection and return his penis to a flaccid state, the scrotal pump is typically again manipulated by the patient in an instructed way to cause fluid transfer from the cylinder, via the valve, back to the reservoir such that deflation of the cylinder is effected thereby resulting in penile flaccidity as desired. For further reference, an example of a known IPP is described in U.S. Pat. No. 4,566,446 to Fogarty, titled "Penile Prosthesis Device."

Known IPPs heretofore have presented several drawbacks to physicians who implant them in patients, and also to the patients themselves. Among these deficiencies are, for example: (i) an unmet need for a reservoir containing a larger fluid volume than known reservoirs, (ii) difficulty in collapsing and folding, or otherwise manipulating, known reservoirs for placement in a patient's abdomen during implantation surgery, (iii) an unmet need for a cylinder containing a larger fluid volume than known cylinders, and (iv) difficulty in collapsing and folding, or otherwise manipulating, known cylinders for placement in a patient's corpora cavernosa during implantation surgery.

Attempts have been made to solve these aforementioned deficiencies with respect to IPP reservoirs through construction of relatively larger spherical or cylindrical elongate reservoirs of generally standard geometric shapes or cross-sections such as, e.g., spherical and cylindrical. An example of such a known reservoir is shown in U.S. Pat. Applic. Pub. No. 2005/0113639 of George, et al., titled "Fluid Reservoirs for Penile Implant Devices and Methods of Manufacturing."

Attempts have also been made to solve the aforementioned deficiencies with respect to IPP cylinders through construction of relatively larger elongate cylinders, analogously to the known reservoirs mentioned above.

Thus, there exists a need for implantable fluid devices that may overcome deficiencies of known devices. In particular, for example, such implantable fluid devices may provide increased fluid volume in an IPP system without increased outer dimensions or an overall profile of the reservoir or cylinder relative to known reservoirs or cylinders. Also, such implantable fluid devices may be easier to surgically implant relative to known reservoirs and cylinders. Thus, these implantable fluid devices of the present invention may allow a physician to more easily collapse and fold them for insertion into the patient's anatomy while affording a greater range of fluid volume compared to known devices. To accomplish these objectives, these implantable fluid devices could be constructed with a novel and heretofore unknown geometric shape or cross-section that increases surface area when inflated or filled, thereby increasing a total available volume. Thus, these implantable fluid devices could accommodate a larger fluid volume than known devices without requiring a larger elongate or cross-sectional area or "footprint"; and these devices could also require relatively less manipulation to fold and insert into the patient's anatomy thereby making surgical implantation procedures faster and more efficient than possible with known implantable fluid devices.

It is to be understood that collectively throughout this description, IPP reservoirs and cylinders are generally termed "implantable fluid devices" although the term is not limited to such reservoirs and cylinders and could include other implantable devices involving fluid containment, exchange, or transfer. Thus, novel aspects of the present invention regarding implantable fluid devices per se will be appreciated by those in the surgical arts to be capable of use in, and beneficial to, virtually any implantable fluid devices—even those outside of IPP technologies.

SUMMARY OF THE INVENTION

In accordance with basic aspects of the present invention, an implantable fluid device comprises a flexible fluid chamber capable of being in an inflated state and a deflated state. The chamber has a first end, a second end, and a central longitudinal axis from the first end to the second end. The chamber also has, in cross section when deflated, a plurality of alternating protrusions and intermediate portions about the central longitudinal axis. When deflated, the protrusions have a selected height and the intermediate portions have a selected depth. When inflated, the protrusions have the selected height and the intermediate portions have a selected height.

Also in accordance with basic aspects of the present invention, a method of manufacturing an implantable fluid device comprises steps of: making a mandrel in a shape of a flexible fluid chamber; dipping the mandrel into a selected semi-liquid material to coat the mandrel in a form of the flexible fluid chamber; removing the mandrel so coated from the selected semi-liquid material; curing the semi-liquid material; and removing the flexible fluid chamber thereby created from said mandrel.

Further in accordance with basic aspects of the present invention, another method of manufacturing an implantable fluid device comprises steps of: making a mold in a shape of a flexible fluid chamber; filling the mold with a selected semi-liquid material; curing the semi-liquid material; and removing the flexible fluid chamber thereby created from the mold.

DETAILED DESCRIPTION OF THE INVENTION

Figure 1:
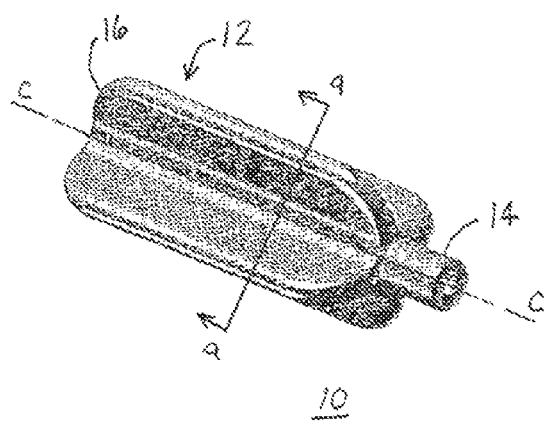
FIG. 1 is a perspective illustration of an example of an implantable fluid device of the present invention, depicting a reservoir for an inflatable penile prosthesis in a deflated state.
Figure 1A:
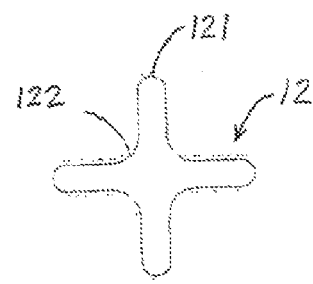
FIG. 1a is a cross-sectional view of the example of an implantable fluid device shown in FIG. 1, taken along reference line a-a.
Figure 2:
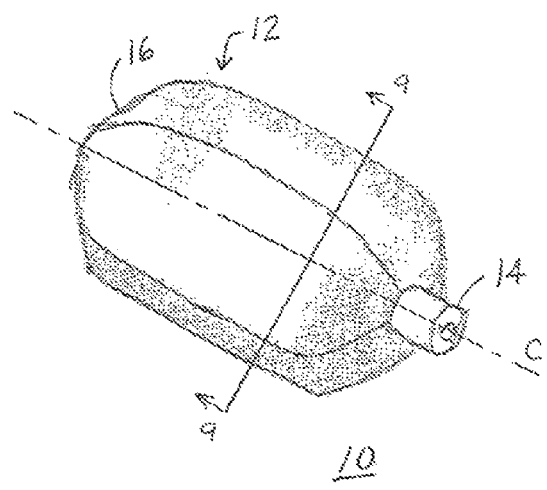
FIG. 2 is a perspective illustration of the example of an implantable fluid device of the present invention, depicting a reservoir for an inflatable penile prosthesis in an inflated state.
Figure 2A:
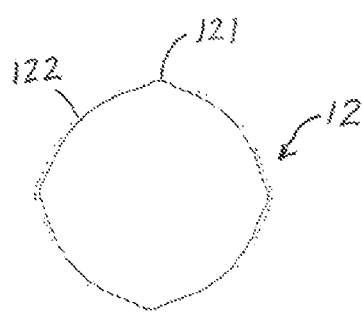
FIG. 2a is a cross-sectional view of the example of an implantable fluid device shown in FIG. 2, taken along reference line a-a.
Figure 3:
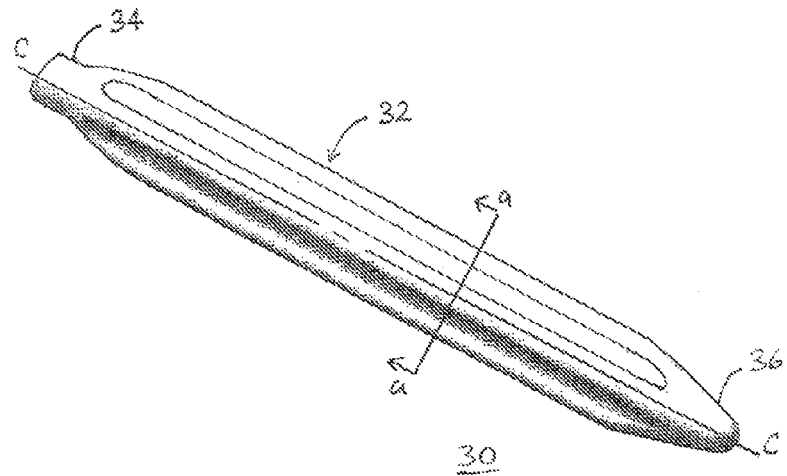
FIG. 3 is a perspective illustration of an example of an implantable fluid device of the present invention, depicting a cylinder for an inflatable penile prosthesis in a deflated state.
Figure 3A:
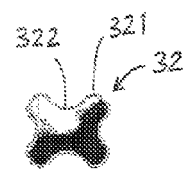
FIG. 3a is a cross-sectional view of the example of an implantable fluid device shown in FIG. 3, taken along reference line a-a.

Illustrated in FIGS. 1, 1a, 2, and 2a is an example of an implantable fluid device of the present invention, depicted as an IPP reservoir 10 (hereinafter, "reservoir 10"). In this example, reservoir 10 could include a flexible fluid chamber 12 capable of being in both a deflated state (FIGS. 1 and 1a) and an inflated state (FIGS. 2 and 2a). Flexible fluid chamber 12 could, in turn, be defined by a first end 14, a second end 16, and a central longitudinal axis C from first end 14 to second end 16. As shown particularly in cross section in FIG. 1a when chamber 12 of example device 10 is deflated, chamber 12 could include a plurality of alternating protrusions 121 and intermediate portions 122 about longitudinal axis C. Protrusions 121 could generally have an approximately uniform selected height, while intermediate portions 122 could generally have an approximately uniform selected depth. Then, as shown particularly in cross section in FIG. 2a when chamber 12 is inflated, protrusions 121 could generally maintain the approximately uniform selected height, while intermediate portions 122 could generally be outwardly deformable to maintain an approximately uniform selected height comparable to protrusions 121. In one embodiment, reservoir 10 could be capable of containing up to 135 ml of a selected fluid.

It is to be appreciated that, as shown particularly in the cross-sectional drawings, implantable fluid devices of the present invention employ what may be characterized as a generally "cloverleaf" profile as opposed to a standard, generally round profile of heretofore known devices. In this configuration, when inflated an implantable fluid device could transform from the "cloverleaf" profile to a generally round profile; and because of additional surface area achievable as compared to a standard round profile, it could achieve greater expansion than devices of round profiles. Thus, it has been discovered that such a "cloverleaf" profile could advantageously allow for both a minimal profile in a deflated state and an increased profile in an inflated. In an example of an IPP cylinder, in particular, both states are highly desirable for concealment when deflated and maximum width or "girth" when inflated.

Figure 4:
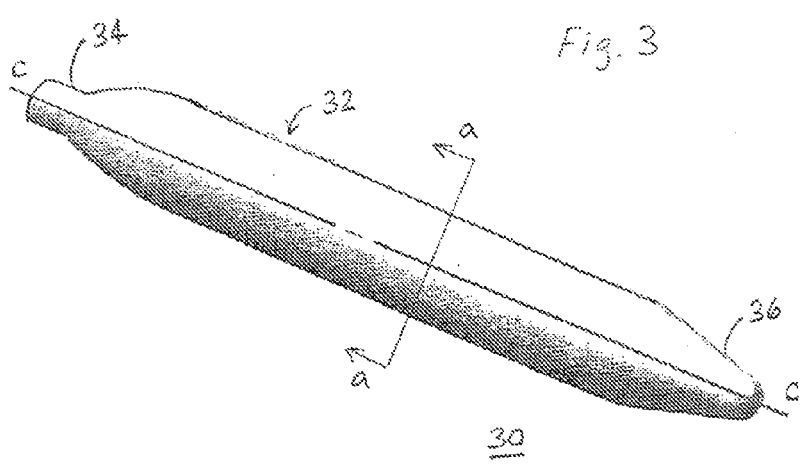
FIG. 4 is a perspective illustration of the example of an implantable fluid device of the present invention, depicting a cylinder for an inflatable penile prosthesis in an inflated state.
Figure 4A:
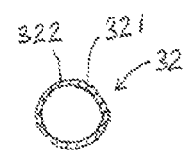
FIG. 4a is a cross-sectional view of the example of an implantable fluid device shown in FIG. 4, taken along reference line a-a.

Illustrated in FIGS. 3, 3a, 4, and 4a is an example of an implantable fluid device of the present invention, depicted as an IPP cylinder 30 (hereinafter, "cylinder 30"). In this example, cylinder 30 could include a flexible fluid chamber 32 capable of being in both a deflated state (FIGS. 3 and 3a) and an inflated state (FIGS. 4 and 4a). Flexible fluid chamber 32 could, in turn, be defined by a first end 34, a second end 36, and a central longitudinal axis C from first end 34 to second end 36. As shown particularly in cross section in FIG. 3a when chamber 32 of example device 30 is deflated, chamber 32 could include a plurality of alternating protrusions 321 and intermediate portions 322 about longitudinal axis C. Protrusions 321 could generally have an approximately uniform selected height, while intermediate portions 322 could generally have an approximately uniform selected depth. Then, as shown particularly in cross section in FIG. 4a when chamber 32 is inflated, protrusions 321 could generally maintain the approximately uniform selected height, while intermediate portions 322 could generally be outwardly deformable to maintain an approximately uniform selected height analogous to protrusions 121 of reservoir 10.

Figure 6:
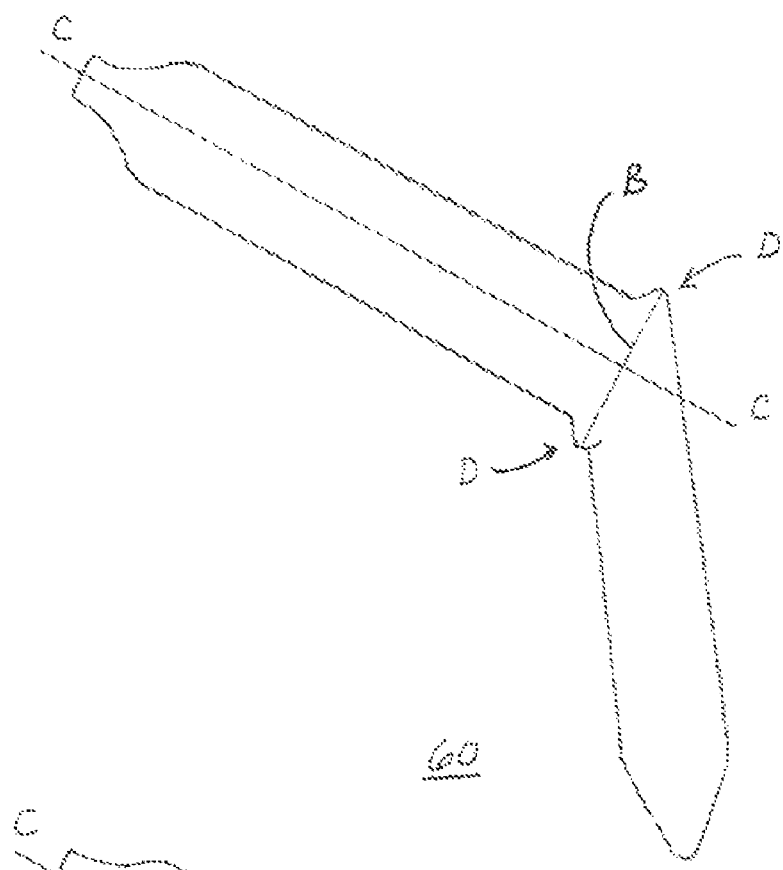
FIG. 6 is a perspective illustration of a known cylinder for an inflatable penile prosthesis, depicting a deflated state.
Figure 6A:
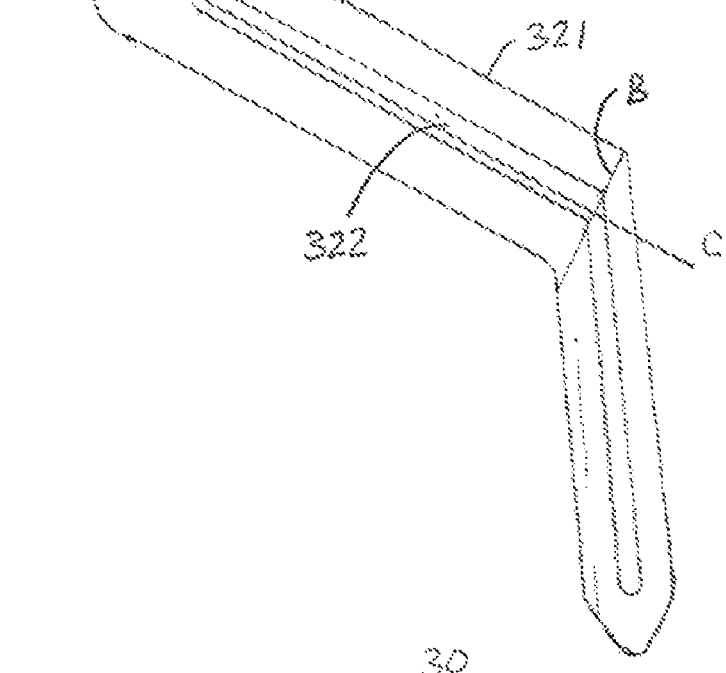
FIG. 6a is a perspective illustration of the example of an implantable fluid device of the present invention, depicting a cylinder for an inflatable penile prosthesis in a deflated state.

As described relative to example reservoir 10, example cylinder 30 could also employ the aforementioned "cloverleaf" profile with its attendant advantages over known devices. In comparing FIGS. 6 and 6a which depict a known deflated cylinder 60 and a deflated cylinder of the present invention 30, respectively, it will be appreciated by those of skill in the IPP art that the aforementioned "cloverleaf" profile could advantageously mute a "dog ear" effect. As shown in FIG. 6, the "dog ear" effect (indicated by opposing protrusions "D" in the drawing) typically occurs when a known cylinder 60 is deflated or at least is not fully inflated (collectively, for purposes of this description, "deflated states"). When the cylinder is bent in such deflated states, protrusions D occur at opposite ends of bending axis B which are generally perpendicular to longitudinal axis C. Historically, these opposing protrusions D together have been characterized as resembling a dog's ear. As known to physicians and patients, this effect can be troublesome both during and after implantation surgery due to localized pressing of protrusions D against corpora cavernosa tissue and resulting localized deformation of that tissue and penis when in such deflated states and not erect. But as shown in FIG. 6a, an example cylinder 30 of the present invention utilizing a "cloverleaf" configuration mutes or inhibits the deleterious "dog ear" effect when in deflated states. This is because the novel "cloverleaf" configuration promotes a non-outward collapsing of the aforementioned alternating protrusions 321 of the deflated cylinder at its bending axis B. Specifically, the aforementioned depth of intermediate portions 322 allows protrusions 321 to collapse non-outwardly. It is to be understood and appreciated, therefore, that such a "cloverleaf" profile in deflated states could allow for both minimal dilation of a patient's corpora cavernosa during implantation surgery, and a minimal profile in the patient when in deflated states.

Figure 5:
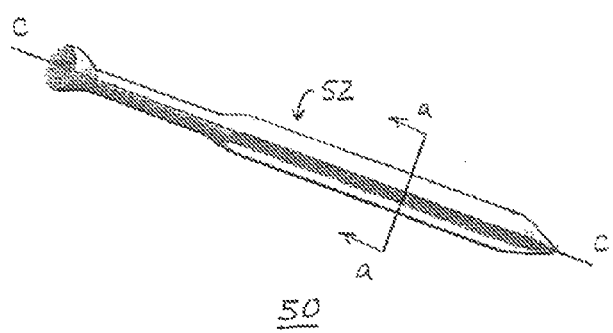
FIG. 5 is a perspective illustration of an example of a mandrel for manufacturing an implantable fluid device of the present invention as a cylinder.
Figure 5A:
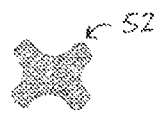
FIG. 5a is a cross-sectional view of the example of a mandrel shown in FIG. 5, taken along reference line a-a.

With reference back to FIGS. 5 and 5a, an implantable fluid device of the present invention represented by example cylinder 30 could be manufactured using any suitable material and fabrication techniques such as by way of an example mandrel 50 having a body 52 as shown in perspective and cross-section, respectively. As is customary for mandrels employed in manufacturing processes, body 52 of example mandrel 50 is in a shape that generally resembles flexible fluid chamber 32 of example cylinder 30. In this manufacturing example, device 30 could be manufactured by dipping (not illustrated) mandrel 50 into a selected semi-liquid material such as a dispersion mixture (not illustrated) of a known bio-material several times to coat mandrel 50 in a form of flexible fluid chamber 32. The selected semi-liquid material could be, as desired or suitable for a particular manufacturing process, a "BIO-FLEX" resin, a medical grade silicone, or an elastic-thermoplastic resin. A curing step between dipping cycles could be approximately 15 minutes, to allow layers of the selected semi-liquid material thus successively deposited on mandrel 50 to partially set. A number of these dipping cycles or "dispersion dips", along with a relative solids content of the dispersion mixture, could determine an optimal wall thickness of implantable fluid device thereby created. Coated mandrel 50 could then be finally removed from the selected semi-liquid material, with the semi-liquid material coated thereon being allowed to finally cure. Then, flexible fluid chamber 32 thereby formed could be removed from body 52 of mandrel 50 for final fabrication processes (not illustrated) as may be desired. It is to be appreciated that, although not illustrated herein, example reservoir 10 could also be manufactured using any suitable material and fabrication techniques such as via a mandrel and a selected semi-liquid material—analogously to example mandrel 50 for example cylinder 30. Alternatively, and again although not illustrated, an implantable fluid device of the present invention represented by example devices 30 and 10 could be produced using a molding process wherein example mandrel 50 could be replaced by a mold into which a suitable biomaterial is injected or otherwise filled.

It is to be appreciated from the foregoing disclosure that the present invention uniquely and advantageously satisfies the long-felt need for implantable fluid devices such as IPP cylinders that have, for example, a desired inflated (erect) profile while also having a relatively minimal deflated (flaccid) profile. Regardless of a given embodiment, the implantable fluid devices of the present invention also satisfy a long-felt need for an easily implantable device in implantation surgery.

While the present invention has been particularly shown and described with reference to the accompanying specification and drawings, it will be understood however that other modifications thereto are of course possible; and all of which are intended to be within the true spirit and scope of the present invention. It should be appreciated that (i) components, dimensions, shapes, and other particulars of example embodiments of the invention aforedescribed may be substituted for others that are suitable for achieving desired results, (ii) various additions or deletions may be made thereto, and (iii) features of the foregoing examples may also be made in combinations thereof. It is also to be understood in general that any suitable alternatives may be employed to provide the implantable fluid devices of the present invention.

Lastly, of course, the choice of compositions, sizes, and strengths of various aforementioned elements of the present invention are all a matter of design choice depending upon intended uses thereof.

Accordingly, these and other various changes or modifications in form and detail of the present invention may also be made therein, again without departing from the true spirit and scope of the invention as defined by the appended claims.

What is claimed is:

1. An inflatable penile prosthesis comprising:
   a body implantable cylinder that is reversibly movable between an inflated state and a deflated state, the body implantable cylinder having opposed first and second ends disposed on a central longitudinal axis, the body implantable cylinder comprising:
   in cross section, when deflated, a plurality of protrusions and a plurality of intermediate portions disposed about the central longitudinal axis, the protrusions disposed a first distance away from the central longitudinal axis and the intermediate portions disposed a second distance away from the central longitudinal axis, the second distance less than the first distance; and
   in cross section, when inflated, the plurality of intermediate portions expand to a distance of approximately the first distance away from the central longitudinal axis;
   wherein the plurality of protrusions and the plurality of intermediate portions combine to form a plurality of leafs disposed around the central longitudinal axis configured to resist outward bending of a wall of the body implantable cylinder.

2. The inflatable penile prosthesis of claim 1, wherein the plurality of protrusions and the plurality of intermediate portions combine to form a cloverleaf shape around the central longitudinal axis that is configured to resist bending of the wall of the body implantable cylinder outward beyond the first distance away from the central longitudinal axis.

3. The inflatable penile prosthesis of claim 2, wherein the plurality of protrusions are configured to collapse toward the plurality of intermediate portions when the wall of the body implantable cylinder bends.

4. An implantable fluid device, comprising:
   a body implantable fluid reservoir reversibly movable between an inflated state and a deflated state, said fluid reservoir comprising a wall that defines a closed first end and a second end having an opening configured to provide fluid communication between an implantable penile prosthesis and said fluid reservoir, and a central longitudinal axis extending from said first end to said second end, said fluid reservoir further comprising:
   in cross section, when deflated, a plurality of alternating protrusions and intermediate portions that terminate at said closed first end and are disposed about said central longitudinal axis, with said protrusions disposed a first distance away from said central longitudinal axis and said intermediate portions disposed a second distance away from said central longitudinal axis, said second distance less than said first distance; and
   in cross section, when inflated, said plurality of intermediate portions expand to a distance of approximately said first distance away from said central longitudinal axis.

5. The implantable fluid device of claim 4, wherein said plurality of alternating protrusions and intermediate portions terminate at a location offset away from said second end.

6. The implantable fluid device of claim 4, wherein said fluid reservoir comprises a hollow reservoir.

* * * * *